(12) United States Patent
Annis (10) Patent No.: US 9,204,848 B2
(45) Date of Patent: Dec. 8, 2015

(54) LOW-DOSE X-RAY BACKSCATTER SYSTEM FOR THREE DIMENSIONAL MEDICAL IMAGING USING A CONVENTIONAL X-RAY TUBE

(71) Applicant: Martin Annis Patent Trust—2009, Cambridge, MA (US)

(72) Inventor: Martin Annis, Cambridge, MA (US)

(73) Assignee: Martin Annis Patent Trust—2009, Cambridge, MA (US)

( * ) Notice: Subject to any disclaimer, the term of this patent is extended or adjusted under 35 U.S.C. 154(b) by 0 days.

(21) Appl. No.: 14/752,862

(22) Filed: Jun. 27, 2015

(65) Prior Publication Data

US 2015/0297156 A1   Oct. 22, 2015

Related U.S. Application Data

(60) Provisional application No. 62/125,530, filed on Jan. 26, 2015.

(51) Int. Cl.
*G01N 23/203* (2006.01)
*A61B 6/00* (2006.01)
*A61B 6/06* (2006.01)

(52) U.S. Cl.
CPC ............... *A61B 6/4071* (2013.01); *A61B 6/06* (2013.01); *A61B 6/4078* (2013.01); *A61B 6/4085* (2013.01); *A61B 6/42* (2013.01); *A61B 6/502* (2013.01); *G01N 23/203* (2013.01)

(58) Field of Classification Search
CPC ... G01N 23/00; G01N 23/203; G01V 5/0025; A61B 6/483
USPC .................................. 378/70, 86, 87
See application file for complete search history.

(56) References Cited

U.S. PATENT DOCUMENTS

| | | | |
|---|---|---|---|
| 4,809,312 A | 2/1989 | Annis | |
| 4,839,913 A | 6/1989 | Annis et al. | |
| 5,692,029 A | 11/1997 | Husseiny et al. | |
| 7,136,453 B2 | 11/2006 | Jupp et al. | |
| 7,561,666 B2 | 7/2009 | Annis | |
| 7,620,150 B1 | 11/2009 | Annis | |
| 8,094,782 B1 | 1/2012 | Annis | |
| 2005/0185756 A1 | 8/2005 | Wang et al. | |
| 2007/0098142 A1 | 5/2007 | Rothschild et al. | |

*Primary Examiner* — Jurie Yun
(74) *Attorney, Agent, or Firm* — Altman & Martin; Steven K Martin (57) ABSTRACT

An x-ray source emits a cone beam to a rotating, x-ray-opaque disc with radial slots. The slots break the cone beam into fan beams that are emitted to an x-ray-opaque plate that produces a scanning x-ray pencil beam as each fan beam moves across a slit in the plate. A backscatter detector is adjacent to the plate. A collimator is adjacent. The pencil beam enters the object space through slits in the detector and collimator. The pencil beam moves rapidly in the y direction in the object space, producing backscatter x-rays from the object. The collimator only passes backscattered x-rays at a selected distance from the detector. Simultaneously, the assemblage of x-ray source, disc, plate, detector, and collimator moves slowly in the x and z directions. The backscattered x-rays passed by the collimator are processed to form planar images at various depths in the object space.

15 Claims, 4 Drawing Sheets

FIG. 5

LOW-DOSE X-RAY BACKSCATTER SYSTEM FOR THREE DIMENSIONAL MEDICAL IMAGING USING A CONVENTIONAL X-RAY TUBE

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING COMPACT DISK APPENDIX

Not Applicable

BACKGROUND OF THE INVENTION

1. Field of the Invention

The present invention relates to x-ray imaging, more particularly, to backscatter x-ray imaging of soft body tissue.

2. Description of the Related Art

X-ray imaging has been done by conventional transmission x-rays for many years. A major limitation to the spatial resolution of transmission x-ray systems is the scattering of the primary beam as it penetrates the breast. The fraction of scattered x-rays to the non-scattered x-rays (the only useful rays in the image) can be more than a factor of 2 for a beam of 30 keV peak at a breast thickness of approximately 5 cm, resulting in a loss of contrast and spatial resolution.

Film imaging has now been largely replaced by digital imaging. This more convenient mode does not produce better spatial resolution but is superior in allowing convenient transmission of the images and manipulation to better evaluate the images.

Still more recent is the development of three-dimensional (3D) systems for breast imaging. These systems use digital tomography/laminography algorithms that produce 3D images that appear at the present time to be better able to detect small cancers of the breast. 3D images are produced by producing approximately 15 to 20 transmission images of a breast from different angles, combining the images, and using an algorithm that chooses selected pixels at a given depth that appear in each of the transmission images and blurring all the other pixels. The resulting blurred 3D image is refined by a series of "maximum likelihood" enhancements that reduce the blurring.

Thermal (infrared) imaging of the breast has a long history. It has recently been proposed to use nano-particles that have been tagged to locate tumor tissue together with external magnetic field excitation to locally heat suspect areas in the breast for imaging and treatment.

The use of backscatter x-ray systems for the inspection of personnel for security purposes is now common. These systems operate at very low exposure levels and are limited to an exposure of 10 micro-Roentgens (µR) by government regulation. The current system will provide more than 1000 times greater x-ray flux to the patient than the security systems, providing image quality never seen before in soft tissue or the lung.

BRIEF SUMMARY OF THE INVENTION

In the system of the present invention, an x-ray source emits a cone beam to a rotating, x-ray-opaque disc with four narrow radial slots. The slots break the cone beam into moving fan beams, which impinge on a x-ray-opaque plate with a narrow slit. As each fan beam moves across the plate, the slit produces a scanning x-ray pencil beam.

A large area x-ray backscatter detector is mounted adjacent to the plate. The detector has a rectangular slit centered on the plate slit so that the pencil beam can pass through the detector uninterrupted. A focusing collimator is mounted adjacent to the detector. The collimator is formed from multiple focusing sheets of radio-opaque material with a planar gap between each pair of sheets. The gap (collimator slit) between the two center sheets is aligned with the detector slit. The pencil beam enters the object space through the detector and collimator slits.

The extended plane of each collimator gap intersects at a common straight line within the object space. This line defines the distance of the imaged plane from the bottom of the collimator. The thickness of the focused slice around the imaged plane is related to the width of the gaps.

The entire assembly, which includes the x-ray source, rotating disc, x-ray-opaque plate, detector, and collimator, moves in a direction transverse to the pencil beam scan. The speed of movement is slow compared to the time required for a single line of data to be recorded such that the assembly moves one pixel transversely during the same time that each single line of pixels is recorded. Thus, an x-ray backscatter image is produced of a single slice of the object.

The imaging of subsequent slices is achieved by moving the assembly relative to the object parallel to the x-ray pencil beam. The assembly moves the thickness of one slice during the same time that the assembly has moved transversely to produce one slice.

The thickness of each of the slices may be modified by replacing the entire focusing collimator with a collimator that has different gap angles.

Objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein.

DETAILED DESCRIPTION OF THE INVENTION

The present application hereby incorporates by reference in its entirety U.S. Provisional Patent Application No. 61/125, 530, on which this application is based.

U.S. Pat. No. 7,620,150, issued to the present inventor and entitled X-ray Backscatter System for Imaging at Shallow Depths, discloses a method of producing images using a backscatter system and is incorporated herein by reference. U.S. Pat. No. 8,094,782, issued to the present inventor and entitled X-ray Backscatter System for Imaging Soft Tissue Regions, also discloses a method of producing images using a backscatter system and is incorporated herein by reference.

The method of the current invention is an improved version of the '782 patent and differs from the '782 patent in several ways. The '782 patent uses backscatter x-rays of the object to produce 2D images of the cancer lesion and the normal tissue simultaneously, while the current invention employs a focusing collimator that allows separate 3D imaging of normal and cancer regions. The current invention achieves the goal of examining a larger area without losing efficiency of detection by using a rapidly moving pencil beam of x-rays in the x direction and moving the long narrow slit slowly transversely in the y direction. The greatly increased penetration of x-rays is accomplished by using a much higher energy (keV) x-ray source, as described in detail below. The choice of 150 keV peak energy for mammography is a major increase over current systems which use about 15 to 20 keV energy. They require this lower energy to achieve the contrast needed to detect lesions. However, the lower energy reduces the efficiency of these systems because of the absorption and scattering of x-rays of this low energy. The high peak energy used in the current invention allows greater penetration, and scattering does not affect the spatial resolution since this is totally determined by the pencil beam diameter.

The current invention also uses a lower power (watts) and higher peak x-ray energy, thus achieving improved penetration and improved contrast at lower cost. The '150 patent is limited to small area regions and shallow depths within those regions. The '782 patent uses backscatter x-rays of the object that images the cancer lesion and the normal tissue simultaneously, while the current invention employs a focusing collimator that allows separate imaging of normal and cancer regions. The current invention achieves the goal of examining a larger area without losing efficiency of detection by using a rapidly moving pencil beam of x-rays in the x direction and moving the long narrow slit slowly in the y direction transversely to the x direction. The greatly increased penetration of x-rays is accomplished by using a much higher peak x-ray energy (keV) x-ray source, as described in detail below. The choice of 150 keV peak energy for mammography is a major increase over current systems which use about 15 to 20 keV energy. They required this lower energy because they used a transmission x-ray system to achieve the contrast needed to detect soft tissue lesions. However, the lower energy reduced the efficiency of these systems because of the absorption and scattering of x-rays of this low energy. The high peak energy used in the current invention allows greater penetration, and scattering does not affect the spatial resolution since this resolution is totally determined by the pencil beam diameter. The current invention also uses a low-power (watts), low-cost x-ray tube instead of the more costly high-power rotating anode tube used in the '782 patent.

The use of the present invention for the imaging of soft tissue breast tumors is described below. The system may be used to simultaneously image micro-calcifications of 200 micron size by using the partial volume effect and the higher x-ray attenuation of these calcifications and the thinner slices that are imaged compared to the prior art systems. The system may also be used for other applications including, but not limited to, the imaging of soft tissue tumors of the lung and imaging of a beating heart.

It is known that lung lesions that are calcified are less likely to be cancer than soft tissue lesions in the lung. Backscatter imaging is uniquely sensitive to this difference because the calcium in the lesions produces very much greater x-ray attenuation than a soft tissue lesion of the same volume.

For imaging of the heart to a depth of more than five cm from the front or back of the patient, backscatter offers great advantages over CT, transmission imaging, and MRI imaging, all of which are too slow to image a beating heart. On the other hand, the current invention uses a rapidly moving pencil beam of x-rays that "stops" the heart motion. Thus, the image is not blurred, but rather records the motion of the beating heart and the larger blood vessels.

A system for use by the present invention is shown in the FIGS. 1-4. The scan is achieved by using the same technique now widely used to produce a pencil beam of x-rays. An x-ray source 12 emits a cone beam 30 with an axis 38 to an x-ray-opaque disc 14 with four narrow radial slots 16 that rotates rapidly perpendicularly to the cone beam axis 38. The slots 16 break the cone beam 30 into moving fan beams 32. The disc 14 is mounted adjacent to an x-ray-opaque plate 18 with a narrow slit 20. The moving fan beams 32 impinge on the plate 18 and, as each fan beam 32 moves across the plate 18, the stationary slit 20 in the plate 18 produces a scanning x-ray pencil beam 34 that scans in the y direction in FIGS. 2 and 3.

Figure 1:
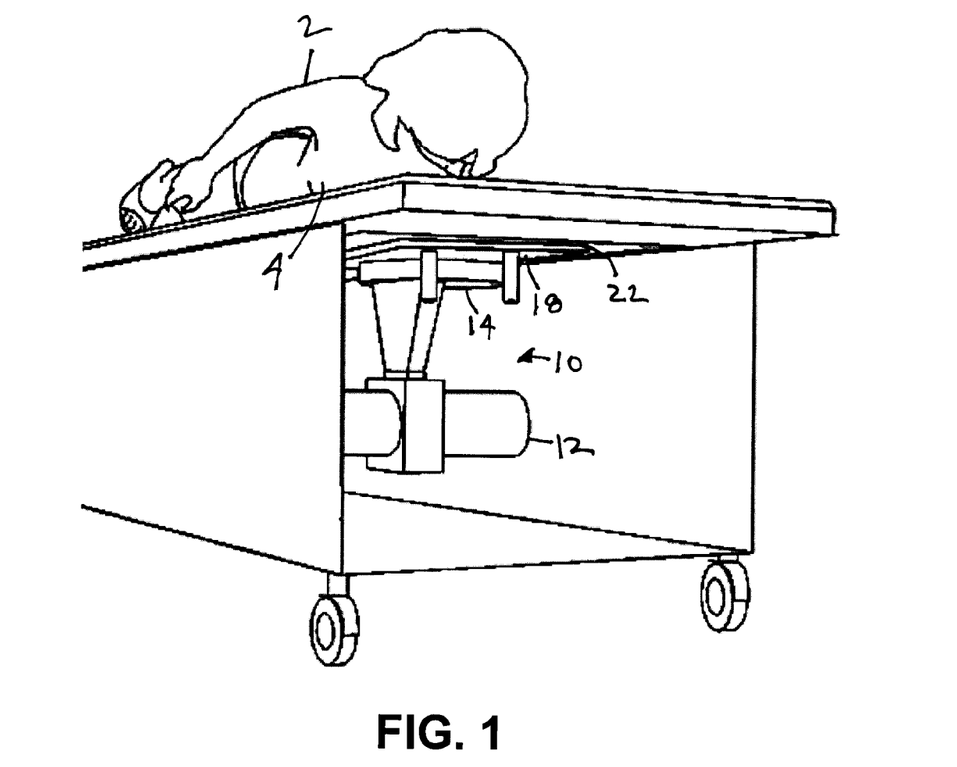
FIG. 1 is a perspective view of a system in use incorporating the present invention.
Figure 2:
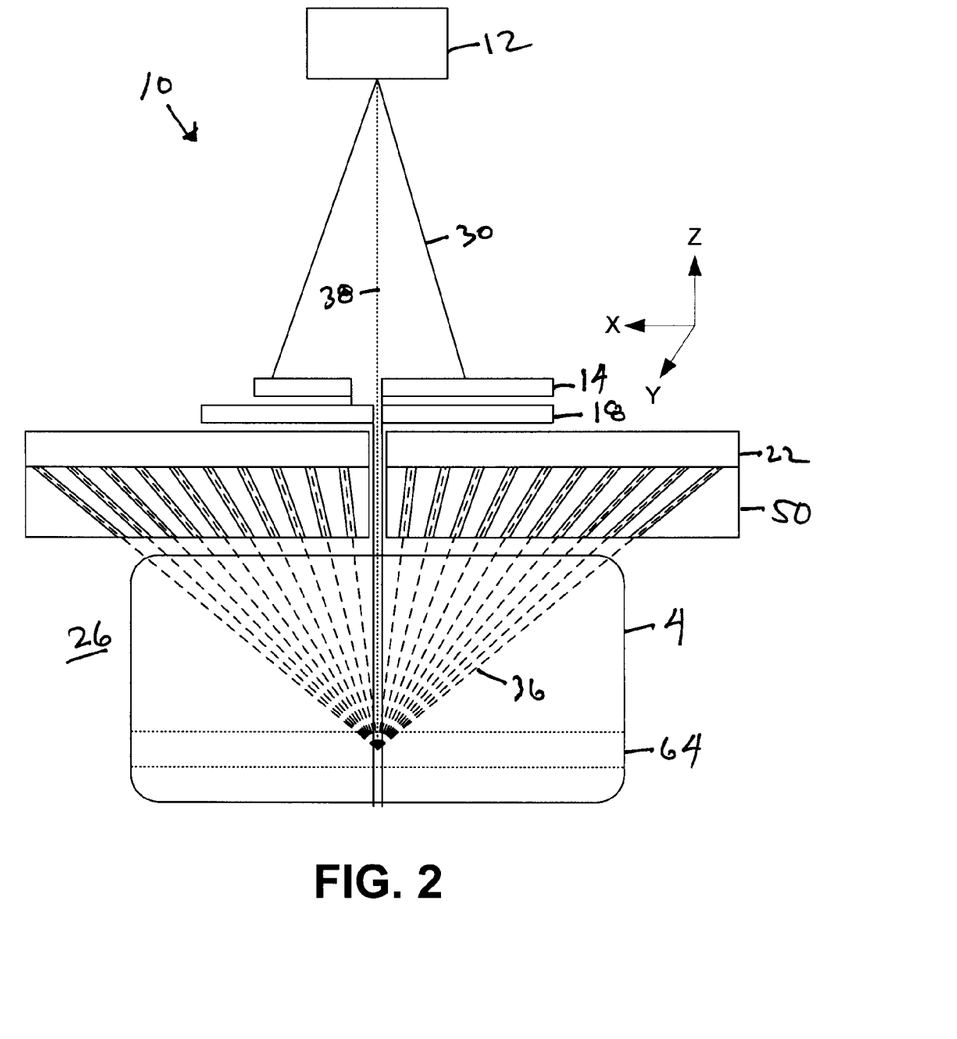
FIG. 2 is an upside down, side cross-sectional view of the system of FIG. 1.
Figure 3:
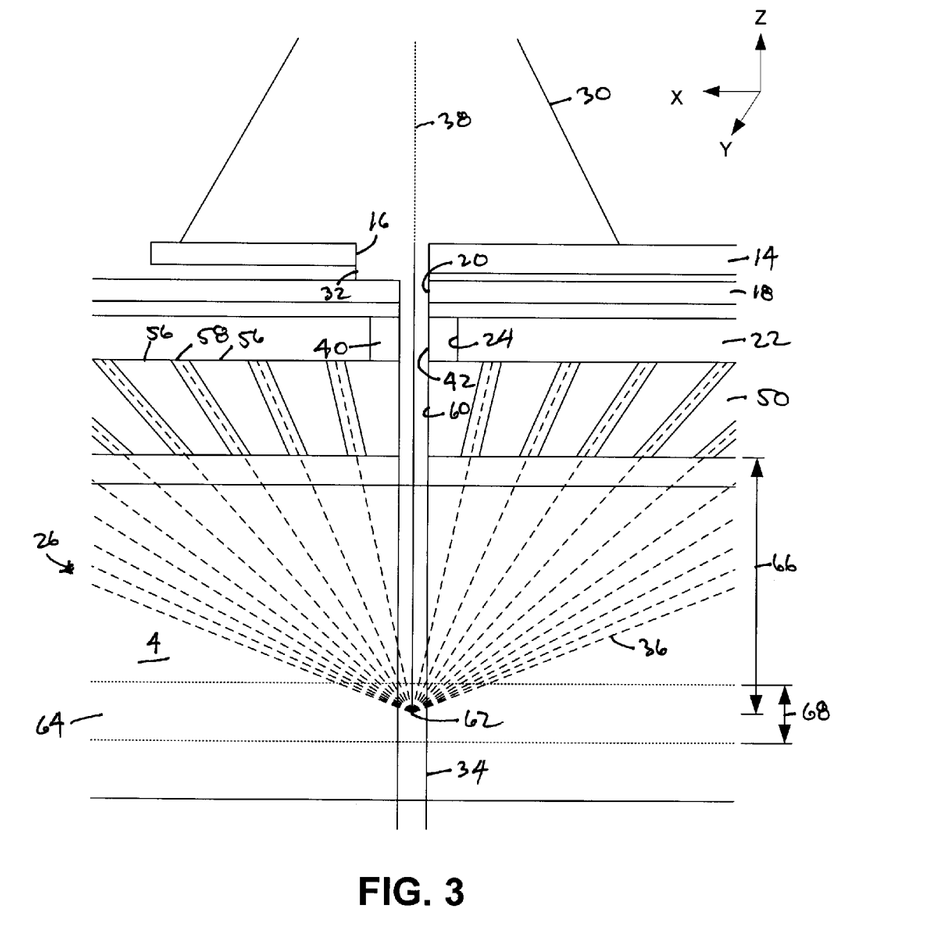
FIG. 3 is an expanded view of the pencil beam generating components of FIG. 2.
Figure 4:
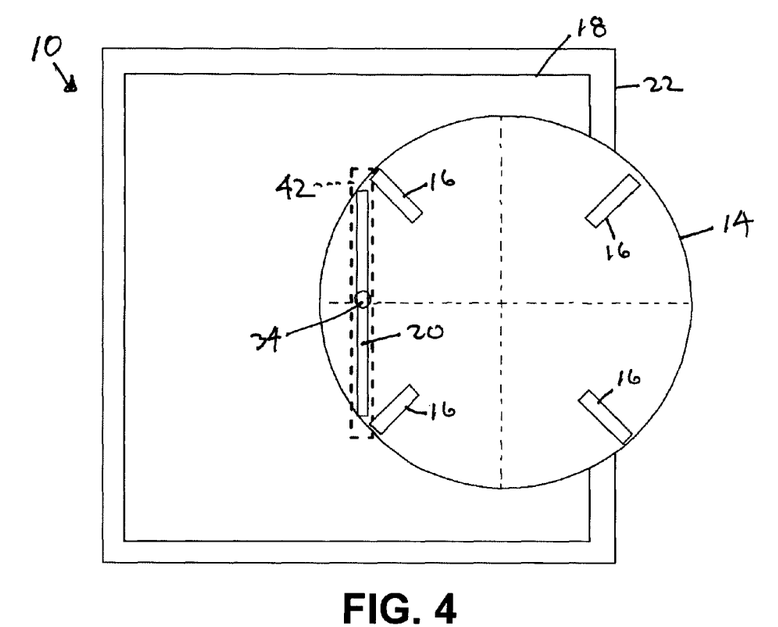
FIG. 4 is a view of the major components of the system of FIG. 1 as viewed from the x-ray source.

A large area x-ray backscatter detector 22 is mounted adjacent to the plate 18. The detector 22 has a rectangular gap 24 centered on the slit 20. The gap 24 is filled by a tungsten plate 40 that has a slit 42 that corresponds to and is aligned with the plate slit 20. The tungsten plate 40 ensures that x-rays scattered directly backwards around a small angle from the pencil beam 34 in a narrow cone of half angle approximately 10° are not detected. These x-rays, if detected, would add "noise" to all of the desired measurements of backscattered rays from the chosen segments along the pencil beam 34. Since the solid angle subtended by the backscatter detector 22 from every point along the pencil beam 34 is very large, this slit 42 does not significantly reduce the usable data. Tungsten, as well as lead, not only shields x-rays, but also has the property that it does not produce any backscatter x-rays that would degrade performance. In addition, tungsten retains its shape.

A focusing collimator 50 is mounted adjacent to the detector 22 and is thick enough, as at 52, to extend to an appropriate distance 54 from the object 4 being imaged. The collimator 50 is formed from multiple focusing sheets 56 with a planar gap 58 extending in the y direction between each pair of sheets 56. The gap 60 between the two center sheets, also referred to as the collimator slit 60, is aligned with the tungsten slit 42.

The pencil beam 34 enters the object space 26 through the tungsten slit 42 and collimator slit 60 without interference from the backscatter detector 22 or collimator 50 on its way into the object space 26. The object space 26 is where the object 4 being imaged resides and, in the remainder of the present specification, the object 4 being imaged is a female breast.

The extended plane of each gap 58 intersects at a common straight line 62 extending in the y direction within the object space 26. This line 62 defines the distance 66 of the imaged plane from the bottom of the collimator 50. The collimator 50 allows only the backscatter x-rays from that selected distance 66 (and a thickness 68 on other side of the selected distance 66) to pass through to the detector 22. All other x-rays are blocked by the collimator 50.

The thickness 68 of the focused slice 64 around the imaged plane, T, is related to the width of the gap 58, $d_i$, between the ith pair of focusing sheets 56, at an angle of $a_i$ with the pencil beam 34, approximately by $T=d_i/\sin(a_i)$.

The entire assembly 10, which includes the x-ray source 12, rotating disc 14, x-ray-opaque plate 18, detector 22, and collimator 50, moves in a direction transverse to the pencil beam 34 scan, the x direction in FIGS. 2 and 3. The speed of movement is slow compared to the time required for a single line of data to be recorded such that the assembly 10 moves one pixel transversely during the same time that each single line of pixels is recorded. Thus, an x-ray backscatter image is produced of a single slice 64 of the object 4.

The imaging of subsequent slices 64 is achieved by moving the assembly 10 relative to the object 4 parallel to the x-ray pencil beam 34, the z direction in FIGS. 2 and 3. The assembly 10 moves a distance T in the direction of the pencil beam 34 the thickness 68 of one slice 64, during the same time that the assembly 10 has moved transversely to produce one slice 64.

Thus, three motions are occurring simultaneously. For example, (1) with the disc 14 rotating at approximately 300 rpm, the 2-mm-square pencil beam moves 20 cm along the plate slit 20 in 0.05 sec in the y direction, producing a single line of data for 200, 1 mm pixels; (2) the transverse motion in the x direction produces 200 lines of data in 0.05×200=10 seconds, or one slice 64 of the image, with 200×200=40,000 pixels; and (3) the motion of the assembly 10 parallel to the pencil beam 34 in the z direction produces five slices 64 of data in 10×5=50 seconds, or the volume of the image, of 40,000×5=200,000 voxels. This example is discussed in more detail below.

The thickness of each of the slices 64 may be modified by replacing the entire focusing collimator 50 with a collimator 50 that has different gap angles. Since the collimator 50 is a single solid element, produced, for example, by a 3D printer, it can be easily changed.

The x-ray exposure and the spatial resolution of the x-ray image may be adjusted by (1) changing the number of slits 16 in the rotating disc 14; (2) adjusting the rotational speed of the disc 14; and (3) adjusting the speed of the transverse and parallel motion of the assembly 10, all to achieve square pixels, the desired intensity of the x-ray image and the desired spatial resolution.

For the breast version of the present invention, the total area of the object space 26 chosen to be scanned by the pencil beam 34 is 20 cm×20 cm, because this is the area of a larger breast. The distance from the x-ray source 12 to the rotating disc 14/plate 18 is at least approximately 30 cm to ensure that the dimension of the pencil beam 34 is conserved while penetrating the 5 cm thick breast and is also always nearly vertical while the pencil beam 34 moves rapidly over the object space 26. In the illustrated embodiment, the maximum angle from the normal to the slit 20 is +/−(10 cm)/(30 cm)=0.33 radians=19°. Since the ratio of the slant distance into the object space 26 is proportional to the cos(19°)=0.945, this is not a big effect.

The size of the pencil beam 34 is a compromise. A larger pencil beam produces more x-ray flux, which is desirable, and a smaller pencil beam produces better spatial resolution, also desirable. A 2 mm×2 mm beam is chosen and sampled twice in both directions, using the Nyquist Theorem, to achieve 1 mm×1 mm pixels. Since the smallest lesions currently seen are about 10 mm in diameter, this resolution will detect and image much smaller lesions than the prior art.

The pencil beam 34 moves very rapidly in a line across the width of the object space 26 in the y direction as each of the four radial slots 16 in the rotating disc 14 crosses over the slit 20 in the plate 18, 20 cm in 0.05 sec=50 msec and the system is sampled 200 times, i.e. every millimeter. Each sample along the narrow slit is 1 mm, so the individual sample time along is 0.05/200=0.0005 sec or 500 μsec.

Simultaneously, the assemblage 10 of x-ray source 12/rotating disc 14/plate 18/backscatter detector 22/focusing collimator 50 moves more slowly in the x direction for 20 cm to produce a single slice in 20 seconds. The detector 22 is sampled 200×200=40,000 times to form a slice image (i.e. twice for each passage of the 2 mm pencil beam 34 over each location, using the Nyquist theorem to double the spatial resolution). In the x direction, the assemblage 10 moves much more slowly, so the pencil beam 34 only translates by 0.5 mm in the x direction while it moves 20 cm in the y direction. The raster scan of one slice 64 of the 20 cm×20 cm region is accomplished in 20 sec.

The assemblage 10 is also moved slowly in the z direction, moving a distance 68 of one slice 64 during the 20-second time to register a slice of data. If five slices 64 are collected, the total time of exposure is 100 seconds.

As will be shown below, the useful imaging depth of the backscatter imaging system is more than 5 cm, which is about the thickness of the compressed breast. For the x-ray peak energy that has been chosen for the example, 150 keV, the difference in contrast between the front of the breast and the back of the breast differs by less than a factor of five. In contrast to the '782 patent, the optimum peak voltage is at least 150 kV since this results in the maximum penetration of the x-ray pencil beam. In addition, in contrast to the '782 patent, the very large contribution of the x-ray backscattered signal from the normal breast tissue surrounding the cancer lesion is not subtracted from the nearly equally large backscattered signal the cancer lesion, plus the small portion of the pencil beam that traverses the cancer lesion, plus the large portion of the pencil beam behind the lesion.

The performance of the pencil beam backscatter system of the present invention is calculated below. The system is optimized to allow the most efficient use of the x-rays emitted by the x-ray source. The calculation assumes parameters that can be simply changed from the chosen ones in order to optimize the design for the application.

The separation of normal soft tissue and tumor soft tissue is determined by the mass absorption coefficients of the two materials. Since cancer tissue has the same elemental composition as normal tissue, the separation of the two materials is only in the different mass attenuation coefficients of the materials, i.e. mainly the density. The compositions of various human tissues according to National Institute of Standards and Technology (NIST) data and taken from Stephen M. Seltzer, *Calculation of Photon Mass Energy-Transfer and Mass Energy-Absorption Coefficients,* 136 Radiation Research, November 1993, at 147-170 are shown in Table I.

TABLE I

| Material | Density (g/cm³) | Composition (Z: fraction by weight) |
|---|---|---|
| Breast Tissue | 1.020 | 1: 0.106000 |
| | | 6: 0.332000 |
| | | 7: 0.030000 |
| | | 8: 0.527000 |
| | | 11: 0.001000 |
| | | 15: 0.001000 |
| | | 16: 0.002000 |
| | | 17: 0.001000 |
| Soft Tissue | 1.060 | 1: 0.102000 |
| | | 6: 0.143000 |
| | | 7: 0.034000 |
| | | 8: 0.708000 |
| | | 11: 0.002000 |
| | | 15: 0.003000 |
| | | 16: 0.003000 |
| | | 17: 0.002000 |
| | | 19: 0.003000 |
| Whole Blood | 1.060 | 1: 0.102000 |
| | | 6: 0.110000 |
| | | 7: 0.033000 |
| | | 8: 0.745000 |
| | | 11: 0.001000 |
| | | 15: 0.001000 |

TABLE I-continued

| Material | Density (g/cm³) | Composition (Z: fraction by weight) |
|---|---|---|
| | | 16: 0.002000 |
| | | 17: 0.003000 |
| | | 19: 0.002000 |
| | | 26: 0.001000 |

The data indicates a difference in density between blood and breast tissue of about 1.060/1.020, or 4%. So it is not unreasonable to expect that tumor tissue may be more dense than normal breast tissue by more than 2% due to the elevated amount of blood characteristic of tumor tissue and also the higher concentration of higher Z elements in blood that increase the mass attenuation coefficient of blood. This more than 2% increase in the difference in x-ray attenuation is apparently what is seen in current mammography images of soft tissue tumors.

The above portion of the separation of normal soft tissue from tumor tissue is not determined by the parameters of the system including the incident flux. It is determined by the density and mass absorption coefficients of the normal and tumor tissue. Thus, to observe the separation of the two kinds of tissue, tumor and normal, there must, in addition, be sufficient x-ray photons per backscattered pixel to establish a standard deviation in the number of photons detected that is small compared to the separation as defined in #1, above. Thus the prior art requires a large incident flux and hence a powerful x-ray source, i.e., a rotating anode x-ray tube. On the other hand, the current invention uses a conventional high-peak x-ray energy (V), low-power (W), low-cost x-ray tube.

The following parameters have been chosen to illustrate the present invention. They may be changed without changing the thrust of the invention. The peak x-ray energy of 150 keV is used. The cross-section of the scanning x-ray pencil beam is assumed to be 2 mm×2 mm. Double sampling in two directions, using the Nyquist theorem, results in a spatial resolution, or pixel size, of approximately 1 mm.

Z is the atomic number of low Z elements that form human tissue.

W is the atomic weight of an element, in g/atomic weight.

Y=½ is the ratio Z/W and is assumed constant.

$\mu e$ is the cross-sectional area per electron for all elements for backward scattering, in cm²/electron.

A=6×10²³ is Avogadro's number, in atoms/atomic weight.

Ne=Y×A is the number of electrons/g for each material.

Dph is the linear dimension of the pin hole and Dpix is the corresponding side of a pixel. Apix=Dpix² is the area of a pixel. The pencil beam cross-sectional area is twice the area of a pixel because the Nyquist theorem applies in both scan directions, x and y.

The diameter of the pencil beam remains very nearly constant while the beam traverses the 5 cm thick breast because the breast 5 cm below the pin hole array is approximately six times closer to the pin hole than the x-ray tube.

Figure 5:
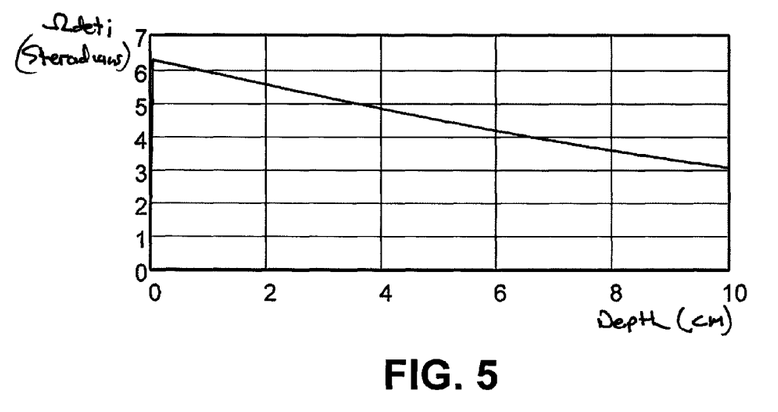
FIG. 5 is a graph showing the efficiency of the x-ray imaging as a function of depth.

The solid angle subtended by the backscatter detector 22 at an average location in the tumor, $\Omega det$, is calculated as:

$$\Omega det_j = 4 \cdot \left[ \int_0^a \int_0^b \frac{z_i}{[x^2 + y^2 + (z_i)^2]^{\frac{3}{2}}} dx\, dy \right]$$

where i=0 . . . 200, $z_i$=0.1×i, a=30 cm, and b=30 cm. a and b are one half of the lateral dimensions of the flat backscatter detector and z is the perpendicular distance from a point in the tumor to the face of the detector. A graph of $\Omega det_j$, shown in FIG. 5, shows that the solid angle is rather constant at a value of approximately 5.5 steradians over all depths to 5 cm.

The solid angle is reduced to the value of $\Omega tot$ to approximately 2 steradians, the minimum in the worst case where the focused slice is furthest from the detector and the flat sheets reduce the solid angle as well.

The total solid angle, $\Omega tot$, subtended by the scattering voxel is about 2 steradians. This solid angle is divided into 10 equal-sized portions, $\Omega fix$, that measure the distance Xrs from this voxel along the corresponding slant angle of the solid angle up to the surface of the backscatter detector. $\Theta s$ is the slant angle between the normal to the surface of the detector and the line from the voxel to the surface for the particular solid angle defined by s=0 . . . 9 and is calculated as:

$$\theta_s = a\sin\left[\frac{(s+1) \cdot \Omega fix}{2 \cdot \pi}\right]$$

Xnorm, Xslant, and Xslanttum are the thicknesses of material (measured in the standard way) between the chosen voxel and the surface of the backscatter detector. Since the x-ray source is relatively far from the pin hole and thus the angle with the normal to the plane of the detector is small, it is assumed that the incident pencil beams are vertical.

Shown below are the thicknesses (g/cm²) used in the calculation. The density of the tumor, denstumor, is assumed to be 1% different from normal breast tissue. With r=0 . . . 100, ftum=0.01, ptum=1+ftum=1.01, where ftum is the fractional difference in density from normal tissue and ptum is the density of the tumor in g/cm³.

$$Xnorm_r := 1 \cdot r$$

$$Xturn_r := Xnorm_r \cdot pturn$$

$$Xslant_{r,s} := \frac{Xnorm_r}{\cos(\theta_s)}$$

$$Xslantturn_{r,s} := \frac{Xturn_r}{\cos(\theta_s)}$$

since the path back to the detector is nearly always through normal tissue.

The matrix below shows the typical photon spectrum of the x-ray source. The second column shows the energy in MeV and the first column is the relative number of photons in the energy interval of 0.015 MeV for the 150 keV x-ray source and so forth.

$$M150 := \begin{pmatrix} 1 & .015 \\ .67 & .030 \\ .55 & .045 \\ .47 & .060 \\ .4 & .075 \\ .33 & .09 \\ .25 & .105 \\ .18 & .120 \\ .11 & .135 \\ .03 & .15 \end{pmatrix}$$

Using data from the NIST, Table II shows the mass attenuation coefficient, μatt, in column two and the mass absorption coefficient, μabs, in breast tissue in column three for x-rays of the energies (MeV) shown in column one.

TABLE II

| Energy (MeV) | μatt (cm2/g) | μabs (cm2/g) |
| --- | --- | --- |
| $1.00000 \times 10^{-3}$ | $3.263 \times 10^{3}$ | $3.255 \times 10^{3}$ |
| $1.03542 \times 10^{-3}$ | $2.975 \times 10^{3}$ | $2.967 \times 10^{3}$ |
| $1.07210 \times 10^{-3}$ | $2.710 \times 10^{3}$ | $2.703 \times 10^{3}$ |
| $1.07210 \times 10^{-3}$ | $2.716 \times 10^{3}$ | $2.709 \times 10^{3}$ |
| $1.50000 \times 10^{-3}$ | $1.088 \times 10^{3}$ | $1.085 \times 10^{3}$ |
| $2.00000 \times 10^{-3}$ | $4.842 \times 10^{2}$ | $4.825 \times 10^{2}$ |
| $2.14550 \times 10^{-3}$ | $3.961 \times 10^{2}$ | $3.946 \times 10^{2}$ |
| $2.14550 \times 10^{-3}$ | $3.983 \times 10^{2}$ | $3.967 \times 10^{2}$ |
| $2.30297 \times 10^{-3}$ | $3.250 \times 10^{2}$ | $3.235 \times 10^{2}$ |
| $2.47200 \times 10^{-3}$ | $2.649 \times 10^{2}$ | $2.636 \times 10^{2}$ |
| $2.47200 \times 10^{-3}$ | $2.686 \times 10^{2}$ | $2.670 \times 10^{2}$ |
| $2.64140 \times 10^{-3}$ | $2.221 \times 10^{2}$ | $2.204 \times 10^{2}$ |
| $2.82240 \times 10^{-3}$ | $1.831 \times 10^{2}$ | $1.818 \times 10^{2}$ |
| $2.82240 \times 10^{-3}$ | $1.845 \times 10^{2}$ | $1.831 \times 10^{2}$ |
| $3.00000 \times 10^{-3}$ | $1.546 \times 10^{2}$ | $1.533 \times 10^{2}$ |
| $4.00000 \times 10^{-3}$ | $6.625 \times 10^{1}$ | $6.540 \times 10^{1}$ |
| $5.00000 \times 10^{-3}$ | $3.407 \times 10^{1}$ | $3.341 \times 10^{1}$ |
| $6.00000 \times 10^{-3}$ | $1.972 \times 10^{1}$ | $1.918 \times 10^{1}$ |
| $8.00000 \times 10^{-3}$ | $8.320 \times 10^{0}$ | $7.899 \times 10$ |
| $1.00000 \times 10^{-2}$ | $4.295 \times 10^{0}$ | $3.937 \times 10^{0}$ |
| $1.50000 \times 10^{-2}$ | $1.378 \times 10^{0}$ | $1.094 \times 10^{0}$ |
| $2.00000 \times 10^{-2}$ | $6.889 \times 10^{-1}$ | $4.394 \times 10^{-1}$ |
| $3.00000 \times 10^{-2}$ | $3.403 \times 10^{-1}$ | $1.260 \times 10^{-1}$ |
| $4.00000 \times 10^{-2}$ | $2.530 \times 10^{-1}$ | $5.792 \times 10^{-2}$ |
| $5.00000 \times 10^{-2}$ | $2.186 \times 10^{-1}$ | $3.666 \times 10^{-2}$ |
| $6.00000 \times 10^{-2}$ | $2.006 \times 10^{-1}$ | $2.881 \times 10^{-2}$ |
| $8.00000 \times 10^{-2}$ | $1.808 \times 10^{-1}$ | $2.470 \times 10^{-2}$ |
| $1.00000 \times 10^{-1}$ | $1.688 \times 10^{-1}$ | $2.478 \times 10^{-2}$ |
| $1.50000 \times 10^{-1}$ | $1.493 \times 10^{-1}$ | $2.734 \times 10^{-2}$ |
| $2.00000 \times 10^{-1}$ | $1.361 \times 10^{-1}$ | $2.945 \times 10^{-2}$ |
| $3.00000 \times 10^{-1}$ | $1.179 \times 10^{-1}$ | $3.173 \times 10^{-2}$ |
| $4.00000 \times 10^{-1}$ | $1.055 \times 10^{-1}$ | $3.260 \times 10^{-2}$ |
| $5.00000 \times 10^{-1}$ | $9.631 \times 10^{-2}$ | $3.281 \times 10^{-2}$ |

The data in Table II is used to construct the following matrices:

$$\mu att150 := \begin{pmatrix} 15 & 1.4 \\ 30 & .34 \\ 45 & .23 \\ 60 & .2 \\ 75 & .19 \\ 90 & .17 \\ 105 & .16 \\ 120 & .16 \\ 135 & .15 \\ 150 & .15 \end{pmatrix}$$

$$\mu abs150 := \begin{pmatrix} 15 & 1.1 \\ 30 & .13 \\ 45 & .05 \\ 60 & .03 \\ 75 & .026 \\ 90 & .025 \\ 105 & .025 \\ 120 & .025 \\ 135 & .026 \\ 150 & .027 \end{pmatrix}$$

μbs is the absorption of the backscattered rays on their way out of the breast into the large backscatter detector. The x-rays that are initially scattered from the narrow pencil beam sometimes penetrate the object and are sometimes scattered backwards toward the x-ray source penetrating the breast and enter the backscatter detector and sometimes may be emitted in the forward direction and thus not detected. They may also be absorbed via the photoelectric effect and removed. They may also be scattered again and again, sometimes ending in the detector. In the absence of any absorption, more than half of the x-rays will end up in the detector. In order to calculate this effect accurately, it would be necessary to perform a Monte Carlo calculation, following many photons as they traverse the object. For the present, a conservative method of estimating this probability is used. It is assumed that if a photon backscattered from the incident pencil beam suffers either an additional scattering or an absorption event on the way back from the chosen voxel in the pencil beam to the detector, the photon does not reach the detector, i.e., μbs=μatt which is always larger than μabs. This is conservative because such a photon has a good probability of reaching the detector after being scattered once.

$$\mu bs150 := \begin{pmatrix} 15 & 1.4 \\ 30 & .34 \\ 45 & .23 \\ 60 & .20 \\ 75 & .19 \\ 90 & .17 \\ 105 & .16 \\ 120 & .16 \\ 135 & .15 \\ 150 & .15 \end{pmatrix}$$

$$Mnorm150_k := \frac{M150_{k,0}}{\sum_k M150_{k,0}}$$

$$\sum_k Mnorm150_k = 1$$

Mnorm is the normalized spectrum of the incident photons. The distance from the x-ray source to the pin hole is 30 cm and the maximum area of the breast is 20×20 cm.

The hole in the template moves rapidly in the y direction a distance of 20 cm in a time of 0.1 sec. In the x direction, the pencil beam moves a distance of one pinhole diameter, Dpix, while the pencil beam moves 20 cm in the y direction in a time of 0.1 sec. Thus, Ty=0.1 sec, Tx=Ty×200=20 and Tz=5× Tx=100 sec, for 5 slices of data.

The matrix below shows the output of a typical x-ray tube as a function of the peak x-ray voltage. The first column is the peak x-ray voltage in kilovolts. The second column is the corresponding emission in R/mA/min at 1 meter from target. The measured radiation exposure, R Roentgens/mA/min, can be found in International Commission on Radiological Protection Publication (1960) in R/mA/min at 1 meter from the target.

$$Roentgen := \begin{pmatrix} 20 & .20 \\ 40 & .37 \\ 60 & .61 \\ 80 & .90 \\ 100 & 1.0 \\ 120 & 1.48 \\ 140 & 2.00 \\ 160 & 2.31 \\ 180 & 2.78 \\ 200 & 3.00 \end{pmatrix}$$

Interpolating from the matrix, Roentgen150=2.15/60 R/sec/mA at 1 meter.

The x-ray source is replaced with an x-ray tube operating at 150 kV and 1800 Watts, or 1800/150=6 mA. So the emission from the x-ray tube, R150, operating at 150 keV peak and with the dimensions of the present system and Tx=20 sec is: R150=Roentgen150(100/30)²×1150×Tz=478 Rs; where Rs is the roentgens at the surface of the template 30 cm from the x-ray source and with a single slice time of exposure of Tx seconds.

Apen=4Apix cm²=4×0.01=0.04 cm² is the area of the pencil beam. This is four times the area of a pixel as the Nyquist theorem is applied. R150 is the entrance exposure to the area of the region used to form the pencil beam of x-rays. Assume that the total area 20×20 cm. Rpb is the flux delivered to the patient via the pencil beam, and Tpb is the time for a single exposure of each area behind the pinhole and is Tpb=Tx (Apen/20²). With Tx=20, Tpb=2×10⁻³ sec.

So the entrance exposure is Rpb150=R150(Apen/20²) =0.05 Roentgens. For a 150 kV peak x-ray tube, this is about ⅐ the skin entrance exposure received from a conventional mammogram.

The number of photons, Mphot150, at 30 cm is $$Nphot150_k := \frac{R150 \cdot 2.15 \cdot 10^9}{.150} \cdot Mnorm150_k$$

photons/cm²/sec/in each energy interval.

$$Nphotsample150_k := Apen \cdot Nphot150_k \cdot Tpb$$

photons/sample/energy interval. The total number of photons per pencil beam, Nphotsampletot, is $$Nphotsampletot150 := \sum_k Nphotsample150_k$$

$$Nphotsampletot150 = 5.48 \times 10^8$$

photons/sample/energy interval. And the number of photons at each energy interval that reach the depth, Xnormal, in the absence of a tumor without interaction is Npbnormal150.

$$Npbnorm150_{k,r} := (Nphotsample150_k \cdot e^{-Xnorm_r \cdot \mu att150_{k,1}})$$

$$Nphotsampletot150depthr_r := \sum_k Npbnorm150_{k,r}$$

$$Nphotsampletot150depthr_{50} = 1.41 \times 10^8$$

i.e., only a factor of 4.

$$\mu e150 := \begin{pmatrix} .015 & 59 \\ .030 & 58 \\ .045 & 57 \\ .060 & 53 \\ .075 & 50 \\ .090 & 42 \\ .105 & 36 \\ .120 & 34 \\ .135 & 33 \\ .15 & 31 \end{pmatrix} \cdot 10^{-27}$$

where column 1 is energy of the incident photon and column 2 is the cross-section for backscatter of the incident photon in cm² per electron×10⁻²⁷.

Eff=0.8 is the approximate efficiency of the backscatter detector in detecting single photons. The efficiency to detect a tumor due to the slight difference of density of a tumor is calculated.

Assuming that there is no tumor, Nbacknormal is the number of photons scattered back from the depth r of normal tissue:

$$Nbacknorm150_r := \sum_k \left( Npbnorm150_{k,r} \cdot \Omega fix + .1 \cdot \mu e150_{k,1} \cdot eff \cdot Ne \cdot \sum_{s=0}^{4} e^{-Xslant_{r,s} \cdot \mu bs150_{k,1}} \right)$$

$$\sum_{r=41}^{50} Nbacknorm150_r = 6.89 \times 10^5$$

photons scattered back from the pencil beam from a 1 cm length of the beam 5 cm from the surface of the breast and reach the surface of the backscatter detector, accounting for all of the attenuations of the pencil beam and the attenuation of the back scattered photons but not accounting for (1) the efficiency of the focusing collimator, approximately 0.8, and (2) the efficiency of the backscatter detector, approximately 0.6. Combining these, the number of photons per sample of a 1 mm×10 mm pixel in the selected slice is Nbacknormal41to50=6.89×10⁵×0.48=6.89×10⁵×0.48=331× 10³ photons per sample of normal tissue and number of photons per sample of tumor tissue is 1.5% greater or Nbacktumor41to50=1.015×Nbacknormal41to50=3.36×10⁵ photons per sample of tumor tissue.

The difference between the number of tumor photons per sample and the number of normal photons is DIFF=Nbacktumor41to50−Nbacknormal41to50=4.96×10³.

The standard deviation in the difference, $SD_{diff}=\sqrt{2}\times SD_{normal}=\sqrt{2}\times\sqrt{N_{backnormal41to50}}=813$. The number of standard deviations between the normal and the tumor cells in a slice of the image at the back of the breast is 4969/813=6.1.

So, in the inspection time of Tz=100 sec, a normal voxel, 1 mm×1 cm, in a slice in the back of the breast 5 cm thick differs from the tumor voxel by six standard deviations.

Thus it has been shown and described an x-ray backscatter system for imaging soft tissue. Since certain changes may be made in the present disclosure without departing from the scope of the present invention, it is intended that all matter described in the foregoing specification and shown in the accompanying drawings be interpreted as illustrative and not in a limiting sense.

What is claimed is:

1. A backscatter scan system for imaging an object, the system comprising:
   (a) in order from back to front, a high-power x-ray source emitting a cone beam with an axis, a rotating x-ray blocking disc having a plurality of radial disc slots and rotating perpendicularly to the cone beam axis, an x-ray blocking plate with a plate slit, an x-ray detector with a detector slit aligned with the plate slit, a focusing collimator having a collimator slit aligned with the detector slit, and an object space having a length, a width, and depth, and adapted to receive the object;
   (b) the x-ray source emitting the cone beam to the disc with a peak energy greater than 50 KeV, the disc slots emitting a moving fan beam to the plate, the plate slit emitting a scanning pencil beam as the disc slots traverse the plate slit, the pencil beam passing through the detector slit and the collimator slit into the object space;
   (c) an assemblage of the x-ray source, the disc, the plate, the detector, and the collimator moving slowly in a first direction the length of the object space;
   (d) the pencil beam traversing across the object space in a line in a second direction the width of the object space, the second direction being generally orthogonal to the first direction, the pencil beam traversing the object space a plurality of times in a plurality of the lines as the assemblage moves the length of the object space;
   (e) the collimator receiving backscattered x-rays from the object space and permitting only those backscattered x-rays originating a selected distance in a third direction from the detector to pass, the third direction being generally orthogonal to the first direction and the second direction;
   (f) the detector receiving the backscattered x-rays passed by the collimator to produce a plurality of line signals from the pencil beam lines at the selected distance, whereby the plurality of line signals represents a single slice of the object space at the selected distance;
   (g) the assemblage moving slowly in the third direction whereby a plurality of slices of the object space is produced; and
   (h) a processor forming a plurality of slice images from the plurality of line signals.

2. The backscatter scan system of claim 1 wherein the collimator is comprised of sheets of radio-opaque material with planar gaps therebetween, the planes of the gaps intersecting at a line extending in the second direction at the selected distance from the detector.

3. The backscatter scan system of claim 2 wherein the collimator is produced by a 3D printer.

4. The backscatter scan system of claim 1 wherein the object is any soft tissue region in a human body.

5. The backscatter scan system of claim 1 wherein the object is a soft tissue region in a breast of a human patient and the breast is compressed into the chest by the weight of the patient during imaging.

6. The backscatter scan system of claim 1 wherein said system simultaneously produces images of soft tissue lesions and micro calcifications.

7. The backscatter scan system of claim 1 wherein the object space is approximately 20 cm long, approximately 20 cm wide, and approximately 5 cm deep, the distance from the x-ray source to the disc is at least 20 cm, and the pencil beam is less than approximately 2 mm by 2 mm in cross-section.

8. The backscatter scan system of claim 7 wherein the pencil beam scans one line in 0.1 sec and the assemblage moves the length of the object space in approximately 10 sec.

9. The backscatter scan system of claim 8 wherein the assemblage moves the depth of the object space in approximately 10 sec.

10. The backscatter scan system of claim 1 wherein the x-ray source is of the rotating anode type.

11. A method of imaging an object comprising the steps of:
    (a) providing, in order from back to front, a high-power x-ray source emitting a cone beam with an axis, a rotating x-ray blocking disc having a plurality of radial disc slots and rotating perpendicularly to the cone beam axis, an x-ray blocking plate with a plate slit, an x-ray detector with a detector slit aligned with the plate slit, a focusing collimator having a collimator slit aligned with the detector slit, and an object space having a length, a width, and depth, and adapted to receive the object;
    (b) the x-ray source emitting the cone beam to the disc with a peak energy greater than 50 keV, the disc slots emitting a moving fan beam to the plate, the plate slit emitting a scanning pencil beam as the disc slots traverse the plate slit, the pencil beam passing through the detector slit and the collimator slit into the object space;
    (c) moving an assemblage of the x-ray source, the disc, the plate, the detector, and the collimator slowly in a first direction the length of the object space;
    (d) the pencil beam traversing across the object space in a line in a second direction the width of the object space, the second direction being generally orthogonal to the first direction, the pencil beam traversing the object space a plurality of times in a plurality of the lines as the assemblage moves the length of the object space;
    (e) the collimator receiving backscattered x-rays from the object space and permitting only those backscattered x-rays originating a selected distance in a third direction from the detector to pass, the third direction being generally orthogonal to the first direction and the second direction;
    (f) the detector receiving the backscattered x-rays passed by the collimator to produce a plurality of line signals from the pencil beam lines at the selected distance, whereby the plurality of line signals represents a single slice of the object space at the selected distance;
    (g) the assemblage moving slowly in the third direction whereby a plurality of slices of the object space is produced; and
    (h) forming a plurality of slice images from the plurality of line signals.

12. The method of claim 11 wherein the collimator is comprised of sheets of radio-opaque material with planar gaps therebetween, the planes of the gaps intersecting at a line extending in the second direction at the selected distance from the detector.

13. The method of claim 11 wherein the object space is approximately 20 cm long, approximately 20 cm wide, and approximately 5 cm deep, the distance from the x-ray source to the disc is at least 20 cm, and the pencil beam is less than approximately 2 mm by 2 mm in cross-section.

14. The method of claim 11 wherein the pencil beam scans one line in 0.1 sec, the assemblage moves the length of the object space in approximately 10 sec, and the assemblage moves the depth of the object space in approximately 10 sec.

15. The method of claim 11 wherein the x-ray source is of the rotating anode type.

* * * * *